(12) United States Patent
Shapiro et al.

(10) Patent No.: US 8,316,862 B2
(45) Date of Patent: Nov. 27, 2012

(54) DEVICES, SYSTEMS AND METHODS FOR MAGNETIC-ASSISTED THERAPEUTIC AGENT DELIVERY

(75) Inventors: Benjamin Shapiro, Washington, DC (US); Isaac B. Rutel, Choctaw, OK (US)

(73) Assignees: University of Maryland, College Park, MD (US); University of Oklahoma, Norman, OK (US)

( * ) Notice: Subject to any disclaimer, the term of this patent is extended or adjusted under 35 U.S.C. 154(b) by 358 days.

(21) Appl. No.: 12/712,182

(22) Filed: Feb. 24, 2010

(65) Prior Publication Data

US 2010/0212676 A1 Aug. 26, 2010

Related U.S. Application Data

(60) Provisional application No. 61/155,223, filed on Feb. 25, 2009.

(51) Int. Cl.
*A61B 19/00* (2006.01)
*A61B 17/52* (2006.01)
*A61N 2/10* (2006.01)
(52) U.S. Cl. .............................. 128/899; 600/9; 604/20
(58) Field of Classification Search .................. 128/899; 335/209–306; 600/9, 11, 12; 604/20
See application file for complete search history.

(56) References Cited

U.S. PATENT DOCUMENTS

| 6,015,377 | A  | * | 1/2000  | Brown et al. ..................... 600/9 |
| 6,562,019 | B1 |   | 5/2003  | Sell |
| 6,617,153 | B2 |   | 9/2003  | Kuehnle et al. |
| 6,689,044 | B2 | * | 2/2004  | Kirschabum ..................... 600/9 |
| 2002/0133115 | A1 |   | 9/2002  | Gordon et al. |
| 2003/0120202 | A1 |   | 6/2003  | Gordon |
| 2005/0192478 | A1 |   | 9/2005  | Williams et al. |
| 2005/0271732 | A1 |   | 12/2005 | Seeney et al. |
| 2009/0287036 | A1 | * | 11/2009 | Shapiro et al. .................. 600/12 |
| 2011/0054237 | A1 | * | 3/2011  | Shapiro et al. .................. 600/12 |

FOREIGN PATENT DOCUMENTS

WO 2009086071 A2 7/2009

OTHER PUBLICATIONS

Search Report and Written Opinion for International Patent Application No. PCT/US2010/032238; Nov. 8, 2010.

* cited by examiner

*Primary Examiner* — Thomas J Sweet
*Assistant Examiner* — Kaylee Wilson
(74) *Attorney, Agent, or Firm* — Seyfarth Shaw LLP; Nigamnarayan Acharya

(57) ABSTRACT

Devices, systems and methods for magnetically assisted agent delivery are included. These devices, systems, and methods make use of a plurality of magnets or magnetic configuration. Two magnets are arranged such that the two magnetic fields overlap and can cancel at the location of the desired node point without canceling around that point.

26 Claims, 5 Drawing Sheets

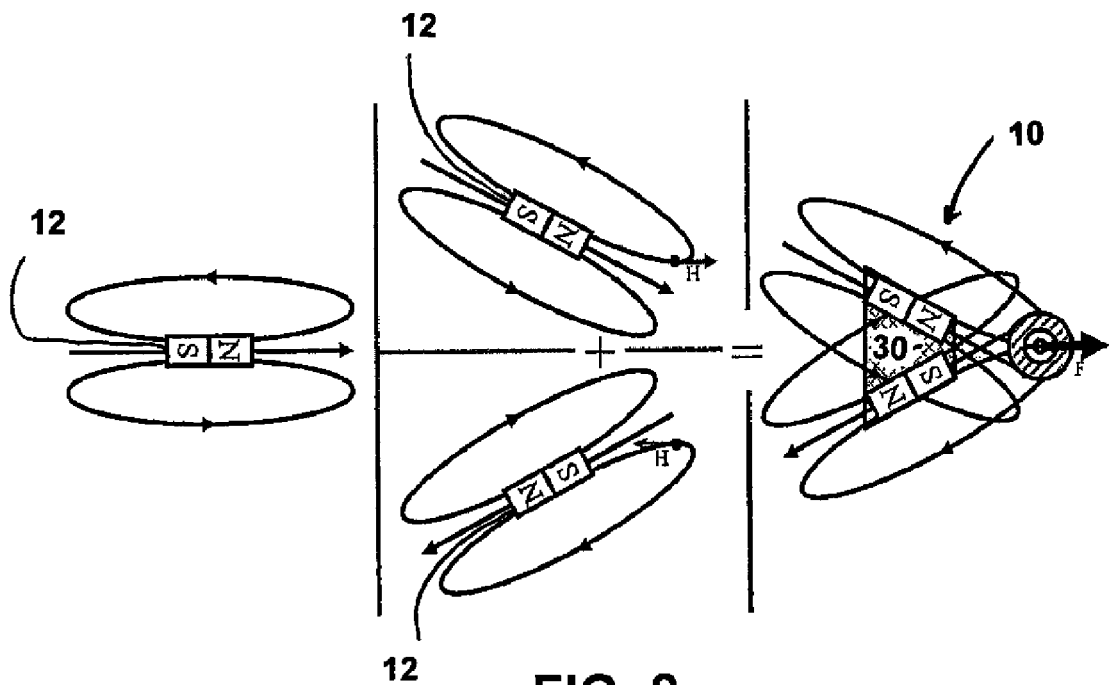
FIG. 2
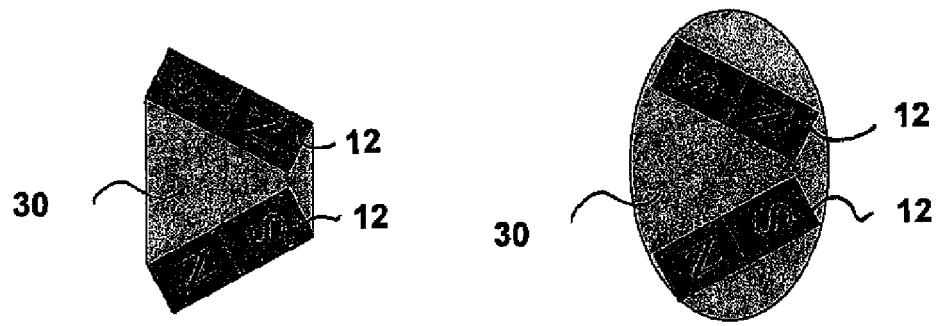
FIG. 3A  FIG. 3B

DEVICES, SYSTEMS AND METHODS FOR MAGNETIC-ASSISTED THERAPEUTIC AGENT DELIVERY

PRIOR RELATED APPLICATION DATA

This application claims priority to U.S. Provisional Patent Application Ser. No. 61/155,223, filed Feb. 25, 2009, which is incorporated by reference.

TECHNICAL FIELD

This application relates generally to the field of therapeutic agent delivery, and more particularly to magnetic-assisted delivery of one or more therapeutic agents.

BACKGROUND

In conventional magnetic drug delivery, magnetically-responsive objects coated by or containing therapeutic agents are injected systemically and are then focused to targets in the body by applied magnetic fields. This can become useful for treatment of cancer, stroke, infection and other diseases because it allows therapy to be concentrated to disease sites (solid tumors, blood clots, infections) while keeping systemic concentrations low (thus minimizing side effects). The magnetically-responsive objects can be micro- or nano-scale iron oxide or other particles coated appropriately to be bio-compatible and therapeutically effective. Sub-micron particles are small enough to pass from the blood to the surrounding tissue through blood vessel walls. Other objects besides particles, such as polymer, microsphere, micelle, and nano-capsule delivery systems, can also be made magnetic or attached to magnetic particles and then used as magnetic carriers.

There is always a need for improved devices, systems, and methods for magnetic agent delivery. It is to this need, among others, that this disclosure is directed.

SUMMARY

This application discloses devices, systems and methods for magnetically assisted agent delivery. One exemplary embodiment of the device can make use of magnetic elements or magnets that may be capable of generating magnetic fields. Typically, a single magnet can have field lines around it. The magnet can be set at an angle that creates magnetic fields along the horizontal x-axis at a desired node location. A second magnet, with an aligned or opposite polarity, can be placed and angled in a configuration with respect to the first magnet so that the magnetic field is equal and opposite (along the minus x-axis) at the desired node location. In this example, these two magnets are arranged such that the two magnetic fields overlap and can cancel at the location of the desired node point without canceling around that point. In one embodiment, a local magnetic field minimum can be created with a higher magnetic field surrounding the node. The magnetic fields can create forces and can act on magnetic, paramagnetic, ferrimagnetic, ferromagnetic, or superparamagnetic that can point outwards from the central region between magnets. Another exemplary embodiment includes a system, which incorporates the magnetic configuration of the devices.

In operation and use, one exemplary embodiment includes a method for directing an agent into or through material by positioning a magnetic configuration having a plurality of magnets, wherein a first magnet in the plurality of magnets produces a first magnetic field; a second magnet in the plurality of magnets produces a second magnetic field. The first magnet and the second magnet define a central space between the first and the second magnet. The first magnetic field and the second magnetic field overlap to create a combined field and create a local magnetic field strength minimum outside the central space. The magnetic field in front of the local minimum acts on the agent; and moves the agent with the force into or through the material.

These and other embodiments, aspects, advantages, and features will be set forth in part in the description which follows, and in part will become apparent to those skilled in the art by reference to the following description of the invention and referenced drawings or by practice of the invention. The aspects and features of the invention are realized and attained by means of the instrumentalities, procedures, and combinations particularly pointed out in the appended claims and their equivalents.

BRIEF DESCRIPTION OF THE DRAWINGS

FIG. 2 shows a schematic representation of certain magnetic principles that can be incorporated into specific embodiments.

FIG. 3A shows a central space defined by edges of the plurality of magnets.

FIG. 3B shows a central space defined by the physical space between the magnets that can be defined by the least volume enclosed by a minimal convex shape.

DETAILED DESCRIPTION

Figure 1:
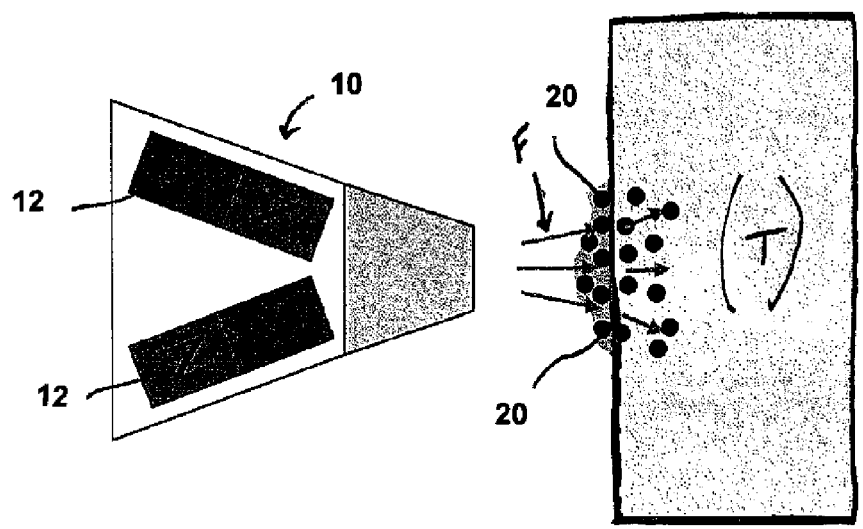
FIG. 1 shows a schematic representation of one exemplary embodiment.

Exemplary embodiments include devices, systems and methods for directing an active agent to a targeted site. One exemplary embodiment is a device 10 for magnetically-assisted delivery of an active agent schematically shown in FIG. 1. One operative principle for magnetically directing the agent (or therapeutics) associated with magnetic particles (e.g. with $Fe_3O_4$ cores), which includes nano-particles, involves an arrangement of magnets 12, which can have a North (N) and a South (S), to direct magnetic-particle formulations or agents 20 from a fluid/gel solution applied away from the targeted site (e.g. on the surface near the targeted site, or in the vicinity of targeted tissues) to the targeted site. Using this principle, the device with its plurality of magnets or magnetic elements can, for example, direct the agent from the fluid/gel solution to the target site. In one embodiment, active agents, e.g. in particles, can be applied away from a target site (e.g. skin on the body) and the device 10 can "push" or apply a force (F) on the particles to the target site (T). In this exemplary embodiment, the device 10 can be used in combination with other aspects of medical technology, including medical nanotechnology.

As shown schematically in FIG. 2, one exemplary embodiment of the device can make use of magnetic elements or magnets that may be capable of generating magnetic fields. Typically, a single magnet can have field lines around it. The magnet can be set at an angle that creates a magnetic field along the horizontal x-axis at a desired node location. A second magnet, with an aligned or opposite polarity, can be placed and angled in a configuration with respect to the first magnet so that the magnetic field is equal and opposite (along the x-axis) at the desired node location. In this example, these two magnets are arranged such that the two magnetic fields overlap and can cancel at the location of the desired node point without canceling around that point. In another example, a local magnetic field minimum can be created with a higher magnetic field surrounding the node. The magnetic forces can act on magnetic, paramagnetic, ferrimagnetic, ferromagnetic, or superparamagnetic agents in the direction from lower to higher magnetic fields and can project outwards from a smaller magnetic field (including possibly H=0) at the local field minimum to a higher magnetic field (e.g. H≠0) neighboring it.

Because of practical considerations (e.g. imperfect magnetic field cancellations) or because of design choices (e.g. smaller or larger region of forces), the location of the magnetic field local minimum may vary. A local minimum may be a region of smaller magnetic field compared to a nearby magnetic field. For example, the field may be smaller in locations nearer to the local minimum. If this location is a point, then this is a local field minimum point. The local minimum does not need to be completely surrounded by higher magnetic field strength. The location can also be a region (e.g. the magnetic field is smaller on an elliptical or other shaped region than in regions outside the peanut). Under this condition, the force on the agent can go from low to high magnetic field.

In one specific example, the device has two magnetic elements 12 in which the first magnet and the second magnet each produce a magnetic field. The magnetic fields are represented by magnetic flux lines that extend from two magnetic poles. The plurality of magnets 12 can be placed at an angle to one another and the magnetic field lines are able to cancel out, or otherwise combine together in a fashion that creates a lower magnetic field strength, so as to form a local magnetic field minimum outside the central space 30.

More particularly, the first magnet and the second magnet define a central space between the first and the second magnet. The central space is the volume defined by the arrangement of the plurality of magnets and is the physical space between the magnets. FIG. 3A shows a central space or region 30 defined by edges of the plurality of magnets. FIG. 3B shows a central space or region 30 defined by the physical space between the magnets that can be the least volume enclosed by a minimal convex shape, wherein the convex shape includes all material points of all the magnets. More particularly, this shape or space can be defined by common mathematical usage in that if any two points are in the volume of the space or region then the line between them is wholly included in the volume of the shape or region. A convex shape is minimal if it is the smallest convex shape that can contain all the material points of all the magnets. The central space is at least the remaining volume in such a minimal convex shape.

The first magnetic field and the second magnetic field overlap to create a combined magnetic field and create a local magnetic field strength minimum outside the central space. The combined magnetic field in front of the local minimum can produce a force on the agent. In certain exemplary embodiments, the magnetic field strength can be between 1 micro-Tesla and 8 Tesla.

Figure 4:
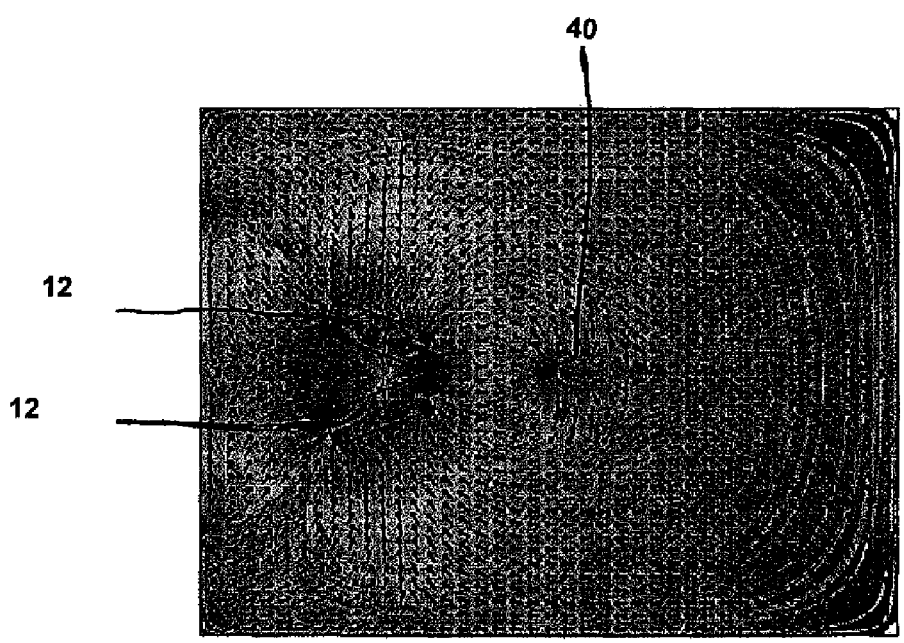
FIG. 4 shows that the magnetic fields can create a combined magnetic field and resulting magnetic forces can spread away from the magnets.

The relative movement between the two magnets can be minimized and the relative angle between the magnets 12 can allow for placement and maximization of the outward force. FIG. 4 shows that the node or local minimum 40 can be described by the intersection of a node curve with the 2D plane. FIG. 4 shows the combined magnetic field from two magnets placed at exemplary angles and the resulting forces spread outward from the local minimum. This region can be shaped, e.g. flattened and widened, to provide an effective force over a desired region, e.g. a region that includes the fluid/gel solution area. In one example, it was found that intuition was effective for determining the angle to position the local minimum. In another example, it was found that automated optimization was effective to determine the angle to position the local minimum. In a third example, it was found that intuition and optimization were effective. It is contemplated that the relative angle between the magnets may vary with the desired specific location and strength of the outward force.

A node can be verified by determining the region in which the magnetic field passes through zero and reverses polarity. The polarity is dependent on the relative direction of the field with respect to the probe. When the polarity is reversed, the magnetic field can flip from approaching the probe from one direction, to approaching it from the opposite direction. A node is a special case of where all fields along a specified vector cancel to give a local field magnitude equal to zero. In the more general case, the same effect can be achieved when a local minimum is attained, that is, where the local field is less than the surrounding magnetic field but not zero. Verification of the local minimum may be measured in a similar method, where the gaussmeter is attached to a control apparatus which systematically measures the magnetic field at defined grid points in the interesting volume. The magnetic field values acquired on the grid can then be analyzed to find a minimum local value (lowest value in comparison to the surrounding magnetic field measurements). The grid coordinates then specify the spatial location of the more generalized minimum required for a working effect. A local minimum can be verified by techniques available to those with ordinary skill in the art.

In one specific example, measurement of the local minimum and force producing region in the device can be accomplished using a step and measure methodology in conjunction with a gaussmeter. The gaussmeter can be secured to the end of a nonmagnetic rod (glass is acceptable) and the magnetic field strength emanating from the combination of the two (or more) secured magnets is measured. Resolution and precision of the measurement is dependent on the gaussmeter and the material to which it is attached. Starting at the closest point between the magnets, the gaussmeter is queried and the field strength is recorded. In some examples, the magnets can touch; however the magnets need not touch. The gaussmeter is then moved in one of the orthogonal axes directions and a new measurement is acquired.

The force of the magnetic interaction depends on the spatial gradient of the magnetic field in the region beyond the node or local magnetic field minimum point or region. This force, which depends on the strength of the magnetic field, can be characterized by measuring the magnetic field of the device beyond the null or local minimum point or region. The step and measure technique with a magnetic field meter (e.g. gaussmeter) can be employed to determine the field (and the force) in the push region of the device (in the outward direction from the device).

The plurality of magnets can be held in relative position to properly align the magnets to produce the local minimum and force-producing region. Any non-magnetic enclosure can be utilized to position the magnets with the appropriate relative angle. The relative angle between the magnets can be influential in creating and positioning the local minimum and force-producing region in the expected or desired region. It is also submitted that the original construction of the magnets themselves may not be homogeneous or constant, and the ability to measure the magnetic field, local minimum and force-producing region can be desired for designing and using the device.

Another exemplary embodiment includes a system which incorporates the magnetic configuration of the devices. This system can direct a magnetic or magnetizable agent into or through material or tissue. The magnetic configuration has a plurality of magnets. Again, the first magnet in a plurality of magnets produces a first magnetic field, and a second magnet in the plurality of magnets produces a second magnetic field. The first magnet and the second magnet define a central space between the first and the second magnet, and the first magnetic field and the second magnetic field overlap and create a local magnetic field strength minimum outside the central space. The combined field in front of the local minimum acts on the agent.

In operation and use, one exemplary embodiment includes a method for directing an agent into or through material by positioning a magnetic configuration having a plurality of magnets, wherein a first magnet in the plurality of magnets produces a first magnetic field; a second magnet in the plurality of magnets produces a second magnetic field. The first magnet and the second magnet define a central space between the first and the second magnet. The first magnetic field and the second magnetic field overlap to create a combined field and create a local magnetic field strength minimum outside the central space. The magnetic field in front of the local minimum acts on the agent and moves the agent with the force into or through the material.

In one example, the method can be analogous to a direct syringe injection except it can deliver therapeutics to regions where a needle cannot easily be used (e.g. the Round Window Membrane) or is more tissue-distributive. The method can be atraumatic, penetrate cells (or microbes), and treat a larger tissue region with a smaller volume of therapeutic agents. It is contemplated that certain embodiments of the device, method, and system will be used to treat or direct therapeutic agents to treat diseases, e.g., heart failure, coronary artery disease, cancer, ear and eye disease, skin infections, etc.

Figure 5:
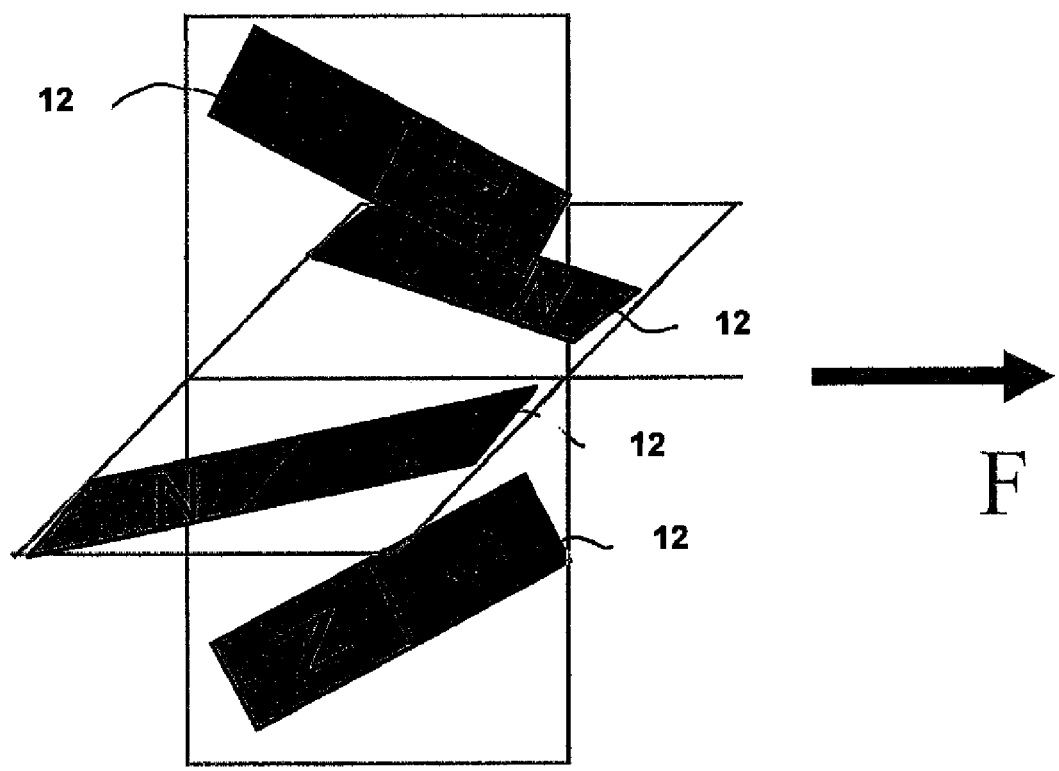
FIG. 5 show exemplary embodiments utilizing more than two magnetic elements.

While some exemplary embodiments make use of two magnets or magnetic elements, it is evident to those with ordinary skill in the art that the device, system, and method can utilize more than two magnets or magnetic elements. It is also possible that a single material can have a plurality of magnets or magnetic elements. Further, it is possible to arrange two or more magnets or magnetic elements to create a local minimum. FIG. 5 shows an exemplary embodiment utilizing more than two magnets or magnetic elements 12, i.e., four magnets or magnetic elements 12.

Figure 6:
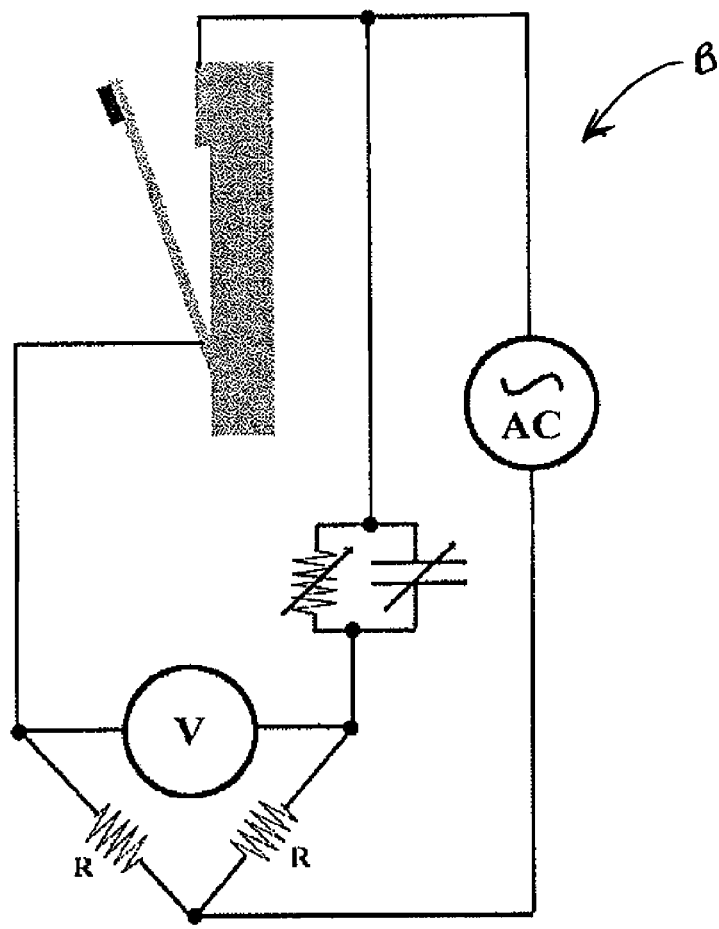
FIG. 6 shows an exemplary bridge circuit B that can provide measurements of the force on the agents.

FIG. 6 shows an exemplary bridge circuit B that can provide measurements of the force on the particles, which includes nanoparticles. A capacitive magnetometer can measure the force on a tip by measuring the capacitance between the tip and base value. Such measurements can be performed. Alternatively, the force on the particles, including nanoparticles, can also be measured by timing and recording the velocities in a standard medium of known viscosities and using the Stokes equation.

The devices may be made of any suitable material (including, e.g., polymeric materials, metals, metal alloys, ceramics, composites, etc.). Although plurality of magnets are depicted as including distinct magnetic fields, it should be understood that the magnetic field generators may or may not be provided as separate and distinct components. As will be understood by those with ordinary skill in the art, the choice of factors, such as size and shape, can degrade or improve the performance of the device or system. In order to secure the magnets, a non-magnetic material is employed to encapsulate or rigidly bind each magnet in the correct position. In cruder examples, wooden wedges in conjunction with glue/polymer based retainers and sufficiently strong tape are an effective binding method to allow for manual/hand held positioning. In another example, the encapsulation of the magnets in a polymer resin material provides a stable and formable shaping method to allow the magnets to be inserted and secured into an arbitrary clamping system for use. The method used for securing/binding the magnets can be non-magnetic (wood, plastic, brass, etc.) in order to minimize the influence of the materials on the shape of the magnetic fields emanating from the magnets. Materials with some magnetically active influence will likely result in deviations from the calculated designs.

The agent should be magnetic or magnetizable (that is associated with magnetic materials). Magnetic materials suitable for site-directed delivery can be incorporated in the coating of an oral dosage formulation or inside the oral dosage formulation and used for site-directed delivery. Alternatively, the agent can be applied topically and then delivered to the targeted site. Further, the agent can be delivered intravenously and then delivered to the targeted site. One of ordinary skill in the art can select suitable modalities to deliver agents to a site away from or proximal to the target site.

Magnetic materials can include paramagnetic, ferrimagnetic, ferromagnetic and superparamagnetic materials (e.g. iron containing compounds), martensitic stainless steels (e.g. 400 series), iron oxides ($Fe_2O_3$, $Fe_3O_4$), neodymium iron boron, alnico (AlNiCo), and samarium cobalt ($SmCo_5$). Moreover, individual magnetic materials have been shown to possess properties that can be combined to achieve localized delivery. Ferromagnetic and superparamagnetic compounds include but are not limited to iron-containing compounds such as martensitic stainless steels (e.g. 400 series), iron and iron oxides ($Fe_2O_3$, $Fe_3O_4$).

If the agent is diamagnetic or if the magnetic material associated with the agent is diamagnetic, then the combined force from the device or system can attract the agent or associated diamagnetic material. Diamagnetic materials, all paired electrons, are slightly repelled by a magnetic field. Diamagnetic properties arise from the realignment of the electron orbits under the influence of an external magnetic field. The use of diamagnetic materials may reverse the interactions with the device or system.

In one exemplary embodiment, the magnetic material is in the form of micron-sized or sub-micron-sized particles. Such particles may be incorporated in micro or nano-particles, optionally the micro or nano-particles contain an active agent to be delivered. Suitable sizes for the magnetic material range from nanometers up to centimeters in cross-sectional diameter or width. In another exemplary embodiment, the magnetic material is larger than 10 microns in length, width, and/or diameter, and may have any shape (e.g. tubes, ellipses, etc.).

As will be known to those with ordinary skill in the art, magnetic particles may be incorporated into the cell or attached to the cell surface by procedures known to those skilled in the art. In certain exemplary embodiments, magnetic particles may be fed to the target cells or temporary pores may be created in the cell membrane of the target cell by electroporation. In other exemplary embodiments, magnetic particles may be attached to the cell surface via an antibody binding to cell membrane receptors or through chemical conjugation of the magnetic particle to the cell membrane.

One or more agents may be formulated alone or with excipients or encapsulated on, in or incorporated into the microparticles or nanoparticles. Suitable agents include therapeutic, prophylactic, and diagnostic agents. These agents include organic or inorganic compounds, amino acids and proteins, sugars and polysaccharides, nucleic acids or other materials that can be incorporated using standard techniques.

In some exemplary embodiments, the magnetic fields may be provided in the form of one or more materials that are magnetic, i.e., that either exhibit a permanent magnetic field or that are capable of exhibiting a temporary magnetic field. The entire device, or selected portions thereof, may be manufactured from the one or more magnetic materials to provide a magnetic field generator. For example, a predetermined quantity of magnetite or an alloy thereof may be included in the construction of the device. Other materials may be utilized in addition to or in place of magnetite to provide the desired magnetic properties. Such materials may be temporary magnetic materials or permanent magnetic materials. Some examples of suitable magnetic materials include, e.g., magnetic ferrite or "ferrite", which is a substance consisting of mixed oxides of iron and one or more other metals, e.g., nanocrystalline cobalt ferrite. However, other ferrite materials may be used.

In one exemplary embodiment, the magnetic field produced by the magnetic field generators is described as static in that magnetic field strength does not vary significantly in time. In another exemplary embodiment, the magnetic field strength may be dynamic in that the magnetic field strength can change over time in response to a controller or other mechanism. The magnetic field strength of some or all of the magnetic fields may be changed over time. Those changes to magnetic field strength may include, e.g., increases and/or decreases in magnetic field strength. In still another exemplary variation, the polarity of either or both of the first and second magnetic fields may be reversed. Such changes in magnetic field strength and/or polarity reversals may be repeated one, two, three, or even more times if the field strength changes and/or polarity reversals enhance delivery of the magnetic particles and their associated active agents to a site.

It is understood that the electromagnets can be used as or in conjunction with the magnets or magnetic elements. An electromagnet is a magnet that is powered with electricity. Unlike a permanent magnet, the strength of an electromagnet can easily be changed by changing the amount of electric current that flows through it. The poles of an electromagnet can even be reversed by reversing the flow of electricity.

If the agents associated with the magnetic particles are cells, the cell may be any biologic cell that is itself capable of exhibiting a magnetic field, being modified to incorporate one or more magnetic particles that include a magnetic field, or that can be attached to a magnetic particle or cell that includes a magnetic particle that exhibits a magnetic field. The cells used in connection with the present invention may be, e.g., endothelial cells, ectoderm-, mesoderm-, endoderm-derived cells. Additionally, any stem or mature cell originating from various primitive cell layers in animals or humans may be modified to be useful in connection with the present invention.

If the device is designed to be deployed to internal (in vivo) locations within a human or animal body, their outer surfaces can be biocompatible. The non-biocompatible magnetic materials within any such device may be contained within or covered by a biocompatible material that does not significantly limit or interfere with the magnetic fields. Biocompatible coatings for use in connection with devices of the present invention may include, e.g., various biocompatible polymers, metals, and other synthetic, natural, or biologic materials.

The above detailed description, the drawings, and the examples, are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

The invention claimed is:

1. A method for directing an agent into or through material, comprising:
   positioning a magnetic configuration having a plurality of magnets, wherein a first magnet in the plurality of magnets produces a first magnetic field; a second magnet in the plurality of magnets produces a second magnetic field; the first magnet and the second magnet define a central space between the first and the second magnet; the first magnetic field and the second magnetic field overlap to create a combined field and create a local magnetic field strength minimum outside the central space; and the combined field in front of the local minimum acts on the agent; and
   moving the agent with the force into or through the material.

2. The method as claimed in claim 1, wherein the agent is magnetic, superparamagnetic, ferrimagnetic, ferromagnetic, or paramagnetic; and is moved by attraction to the higher magnetic field outside the local field minimum, away from the central space.

3. The method as claimed in claim 1, associating a non-magnetic or non-magnetic material with the agent.

4. The method as claimed in claim 1, depositing the agent onto the tissue.

5. The method as claimed in claim 1, further comprising:
   varying an angle to the first and the second magnet to maintain the local minimum directly behind the agent as the agent moves.

6. The method as claimed in claim 1, further comprising:
   calculating a desired angle to position the local magnetic field strength minimum at a desired location and adjusting the magnets so that the angle is the same as the desired angle.

7. The method as claimed in claim 1, further comprising:
   adjusting the angle between the first magnet and the second magnet.

8. The method as claimed in claim 1, further comprising:
   readjusting the angle between the first and the second magnets.

9. The method as claimed in claim 1, wherein either the first magnetic field or the second magnetic field has a field strength of about 1 micro-Tesla to about 8 Tesla.

10. A method for administering an agent to a treatment site, comprising:
    inserting the agent away from the treatment site, wherein the agent is magnetic or magnetizable; and
    guiding the agent to the treatment site with a magnetic configuration having a plurality of magnets, wherein a first magnet in the plurality of magnets produces a first magnetic field; a second magnet in the plurality of magnets produces a second magnetic field; the first magnet and the second magnet define a central space between the first and the second magnet; the first magnetic field and the second magnetic field overlap to create a combined field and create a local magnetic field strength minimum outside the central space; and the combined field in front of the local minimum acts on the agent.

11. A device for directing an agent that is magnetic or magnetizable, comprising:
a plurality of magnets, wherein a first magnet in the plurality of magnets produces a first magnetic field; a second magnet in the plurality of magnets produces a second magnetic field; the first magnet and the second magnet define a central space between the first and the second magnet; the first magnetic field and the second magnetic field overlap to create a combined field and create a local magnetic field strength minimum outside the central space; and the magnetic field in front of the local minimum applies a force on the agent.

12. The device as claimed in claim 11, wherein the combined field in front of the local minimum repels a magnetic, superparamagnetic, ferrimagnetic, ferromagnetic, or paramagnetic agent.

13. The device as claimed in claim 11, wherein the overlapping magnetic field in front of the local minimum acts on a diamagnetic agent by attracting the diamagnetic agent.

14. The device as claimed in claim 11, wherein the local minimum is a null point.

15. The device as claimed in claim 11, wherein the first magnetic field or the second magnetic field has a field strength of about 1 micro-Tesla to about 8 Tesla.

16. The device as claimed in claim 11, the first magnet and the second magnet are at an angle.

17. The device as claimed in claim 16, wherein the angle between the first magnet and the second magnet is adjustable.

18. The device as claimed in claim 11, wherein the first magnetic field and the second magnetic field are static fields.

19. The device as claimed in claim 11, wherein the agent is a diamagnetic agent and is moved by repulsion away from the higher magnetic field outside the local field minimum, towards the central space.

20. A system for directing an agent into or through tissue, comprising:
a) an agent that is magnetic or magnetizable; and
b) a magnetic configuration having a plurality of magnets, wherein a first magnet in the plurality of magnets produces a first magnetic field; a second magnet in the plurality of magnets produces a second magnetic field; the first magnet and the second magnet define a central space between the first and the second magnet; the first magnetic field and the second magnetic field create a combined field and create a local magnetic field strength minimum outside the central space; and the combined field in front of the local minimum applies a force on the agent.

21. The system as claimed in claim 20, wherein the combined field in front of the local minimum repels a magnetic, superparamagnetic, ferrimagnetic, ferromagnetic, or paramagnetic agent.

22. The system as claimed in claim 20, wherein the first magnet or the second magnet is electromagnetic.

23. The system as claimed in claim 20, wherein the first magnetic field or the second magnetic field has a strength of about 1 micro-Tesla to about 8 Tesla.

24. The system as claimed in claim 20, wherein the first magnet and the second magnet have opposite polarities.

25. The system as claimed in claim 20, wherein the first magnet and the second magnet are at an angle; and the angle between the first magnet and the second magnet is adjustable.

26. The system as claimed in claim 20, wherein the first magnetic field and the second magnetic field are static fields.

* * * * *